United States Patent
Bonn

(10) Patent No.: US 12,213,724 B2
(45) Date of Patent: *Feb. 4, 2025

(54) CUTTING ELECTRODE ENHANCEMENT FOR LAPAROSCOPIC ELECTROSURGICAL DEVICE

(71) Applicant: Covidien LP, Mansfield, MA (US)

(72) Inventor: Kenlyn S. Bonn, Lafayette, CO (US)

(73) Assignee: Covidien LP, Mansfield, MA (US)

( * ) Notice: Subject to any disclaimer, the term of this patent is extended or adjusted under 35 U.S.C. 154(b) by 13 days.

This patent is subject to a terminal disclaimer.

(21) Appl. No.: 18/116,868

(22) Filed: Mar. 3, 2023

(65) Prior Publication Data

US 2023/0200884 A1  Jun. 29, 2023

Related U.S. Application Data

(63) Continuation of application No. 16/536,578, filed on Aug. 9, 2019, now Pat. No. 11,607,265.

(60) Provisional application No. 62/722,679, filed on Aug. 24, 2018.

(51) Int. Cl.
   *A61B 18/00* (2006.01)
   *A61B 18/12* (2006.01)
   *A61B 18/14* (2006.01)

(52) U.S. Cl.
   CPC .......... *A61B 18/14* (2013.01); *A61B 18/1206* (2013.01); *A61B 2018/00589* (2013.01); *A61B 2018/00601* (2013.01); *A61B 2018/00607* (2013.01); *A61B 2018/0063* (2013.01); *A61B 2018/00702* (2013.01); *A61B 2018/00875* (2013.01); *A61B 2018/1253* (2013.01); *A61B 2018/1412* (2013.01)

(58) Field of Classification Search
   CPC ............... A61B 18/14; A61B 18/1206; A61B 2018/00589; A61B 2018/00607; A61B 2018/1412
   See application file for complete search history.

(56) References Cited

U.S. PATENT DOCUMENTS

| | | | |
|---|---|---|---|
| 5,534,008 A | 7/1996 | Acksel | |
| 5,800,427 A | 9/1998 | Zamba | |
| 6,066,137 A * | 5/2000 | Greep | A61B 18/1402 606/49 |

(Continued)

FOREIGN PATENT DOCUMENTS

| CN | 106137385 A | 11/2016 |
|---|---|---|
| CN | 106491203 A | 3/2017 |

(Continued)

OTHER PUBLICATIONS

European Search Report dated Dec. 18, 2019, corresponding to counterpart European Application No. 19193353.0; 11 pages.

(Continued)

*Primary Examiner* — Joseph A Stoklosa
*Assistant Examiner* — Annie L Shoulders
(74) *Attorney, Agent, or Firm* — Carter, DeLuca & Farrell LLP

(57) ABSTRACT

An electrosurgical electrode for coagulating and cutting tissue includes a main body fabricated from a conductive material, and a conductive blade extending inwardly from an inner surface of the main body. The blade has an edge configured to concentrate RF for cutting tissue.

20 Claims, 3 Drawing Sheets

(56) References Cited

U.S. PATENT DOCUMENTS

| | | | |
|---|---|---|---|
| 7,214,224 | B2 | 5/2007 | Goble |
| 7,892,230 | B2 | 2/2011 | Woloszko |
| 8,070,803 | B2 | 12/2011 | Camedda et al. |
| 8,075,559 | B2 * | 12/2011 | Stewart ............ A61B 17/00008 606/51 |
| 8,398,625 | B2 | 3/2013 | Dickhans |
| 8,398,661 | B2 | 3/2013 | Deland |
| 8,439,910 | B2 | 5/2013 | Greep et al. |
| 8,500,727 | B2 | 8/2013 | Aramayo |
| 8,591,530 | B2 | 11/2013 | Salky |
| 8,597,310 | B2 | 12/2013 | Salky et al. |
| 9,198,689 | B2 | 12/2015 | Dale et al. |
| 11,607,265 | B2 * | 3/2023 | Bonn ..................... A61B 18/14 |
| 2006/0264929 | A1 | 11/2006 | Goble et al. |
| 2008/0097472 | A1 | 4/2008 | Agmon et al. |
| 2009/0171352 | A1 | 7/2009 | Sutter |
| 2011/0054461 | A1 | 3/2011 | Dickhans |
| 2011/0219887 | A1 | 9/2011 | Schiffers et al. |
| 2013/0325046 | A1 | 12/2013 | Terwiske et al. |
| 2016/0175000 | A1 | 6/2016 | Akagane |
| 2016/0278847 | A1 | 9/2016 | Batchelor et al. |
| 2017/0000513 | A1 * | 1/2017 | Conlon .......... A61B 17/320068 |
| 2017/0312018 | A1 | 11/2017 | Trees et al. |
| 2018/0036023 | A1 | 2/2018 | Takei et al. |

FOREIGN PATENT DOCUMENTS

| | | |
|---|---|---|
| EP | 1527745 A2 | 5/2005 |
| EP | 2292172 A1 | 3/2011 |
| EP | 2436330 A1 | 4/2012 |
| JP | 6292685 | 10/1994 |
| JP | 2001518344 A | 10/2001 |
| JP | 2007054665 A | 3/2007 |
| JP | 2009119218 A | 6/2009 |
| JP | 2011050743 A | 3/2011 |
| JP | 2012081055 A | 4/2012 |
| WO | 9917670 A1 | 4/1999 |

OTHER PUBLICATIONS

Australian Examination Report No. 1, dated Mar. 20, 2020, corresponding to counterpart Australian Application No. 2019219781; 3 pages.

Japanese Office Action dated Sep. 2, 2020, issued in corresponding Japanese Application No. 2019-151904, 6 pages.

Canadian Office Action dated Nov. 5, 2020, issued in corresponding Canadian Appln. No. 3,052,178, 4 pages.

Japanese Office Action dated Dec. 2, 2020, issued in corresponding Japanese Appln. No. 2019151904, 3 pages.

Japanese Office Action dated Apr. 2, 2021, issued in corresponding JP Appln. No. 2019151904, 5 pages.

Canadian Office Action dated Jul. 27, 2021, issued in corresponding Canadian Appln. No. 3,052,178, 4 pages.

Chinese Office Action issued in corresponding application CN 201910781047.9 dated Jun. 6, 2022, together with English language translation (17 pages).

* cited by examiner

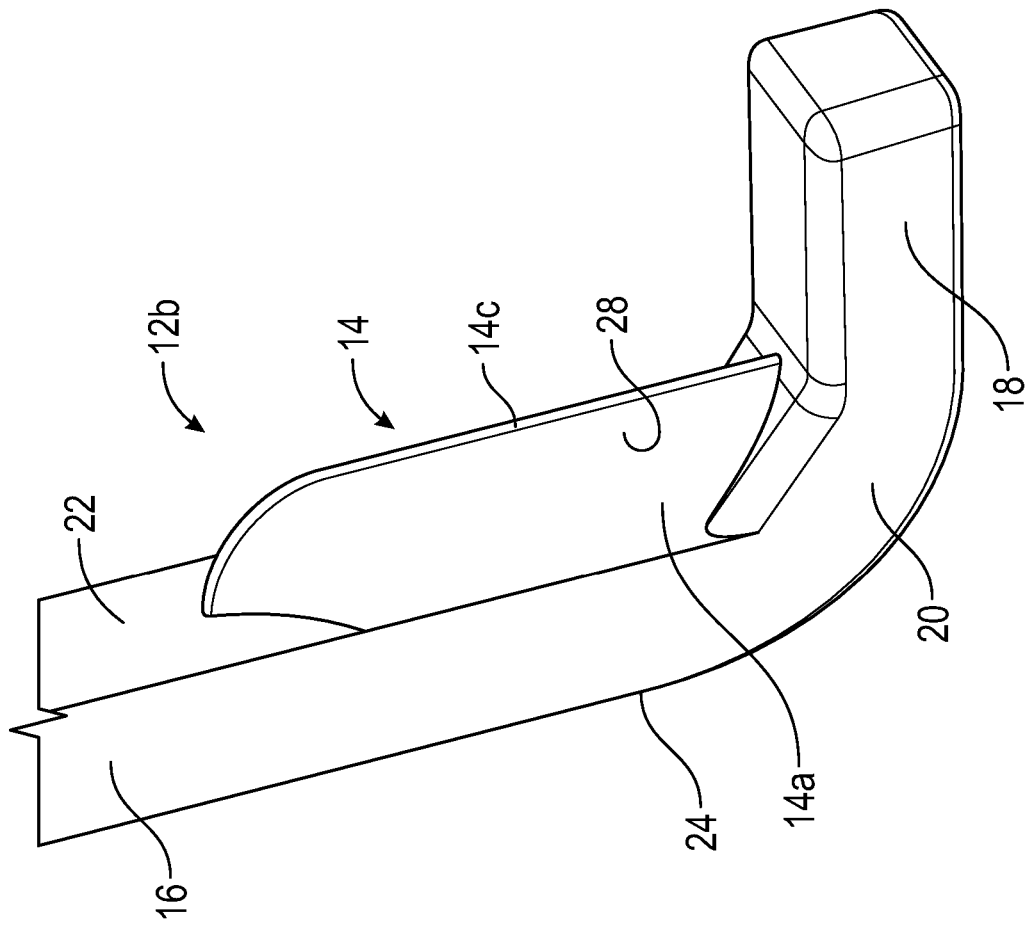
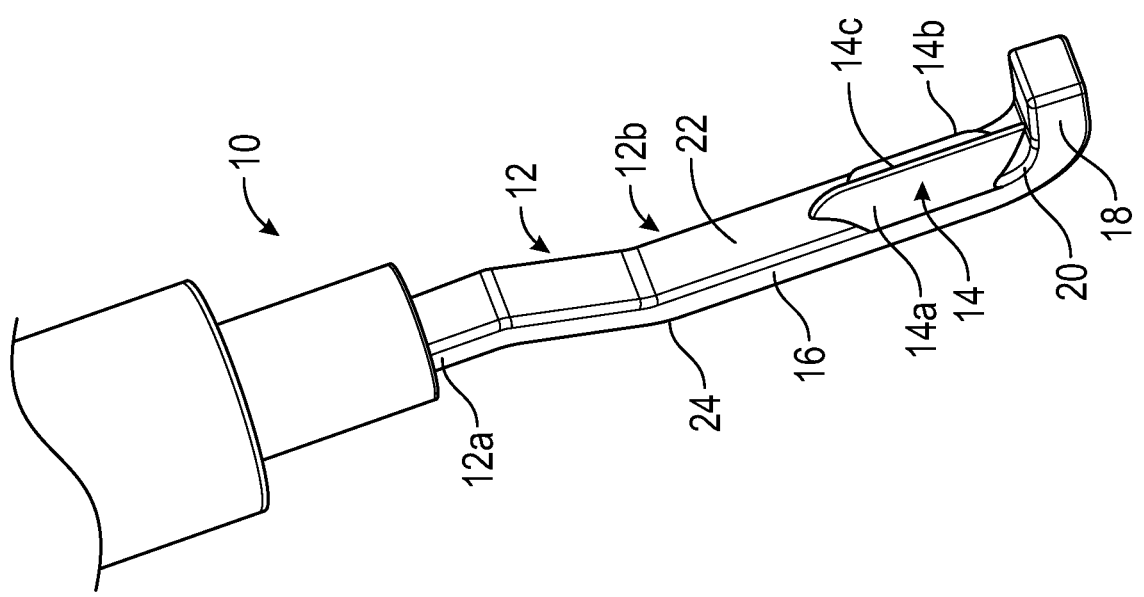

CUTTING ELECTRODE ENHANCEMENT FOR LAPAROSCOPIC ELECTROSURGICAL DEVICE

CROSS-REFERENCE TO RELATED APPLICATIONS

This application is a continuation of U.S. patent application Ser. No. 16/536,578, filed on Aug. 9, 2019, which claims the benefit of the filing date of provisional U.S. Patent Application No. 62/722,679 filed, Aug. 24, 2018.

FIELD

The present disclosure relates to laparoscopic electrosurgical instruments and, more particularly, to an electrosurgical electrode for treating and/or dissecting tissue.

BACKGROUND

Current laparoscopic electrosurgical (e.g., RF) electrodes are configured to provide optimal coagulation performance and mechanical tissue dissection at the expense of the devices ability to transect tissue using electrosurgical "CUT" waveforms. This is intentional as many surgeons need much more coagulation capabilities, but during procedures, it can be observed that the surgeon will tug on tissue in order to transect the tissue plane. When the tissue divides the active electrode then moves out of the field of view so the surgeon then needs to get the electrode end back in to the view of the camera.

SUMMARY

The present disclosure provides a feature for laparoscopic electrodes that includes a surface in a location where RF concentration can be used to improve the tissue transection ability of the device at much reduced power using the CUT or modified CUT waveform while not negatively impacting the coagulation abilities of the device. This will allow surgeons to use less errant motion during dissection, have clean tissue plane transection through a variety of tissue impedances, and minimize thermal spread and tissue charring but not change the typical coagulation usage. Using RF concentration in a place of the electrode that is not typically used for coagulation, the laparoscopic electrode then will effectively do both cutting and coagulation.

In accordance with an aspect of the present disclosure, an electrosurgical electrode is provided for coagulating and cutting tissue. The electrosurgical electrode includes a main body fabricated from a conductive material, and a blade. The main body includes a distal end portion, which has an inner surface, and a curved outer surface configured to coagulate tissue. The blade extends from the inner surface of the distal end portion and has an edge configured to concentrate RF for cutting tissue.

In aspects, the blade may extend inwardly from the inner surface of the distal end portion.

In aspects, the blade may have a pair of opposite side surfaces converging toward the edge.

In aspects, the pair of opposite side surfaces may be coated with a non-conductive material.

In aspects, the edge may be devoid of the non-conductive material.

In aspects, the inner and outer surfaces of the distal end portion may be coated with the non-conductive material.

In aspects, the coating of the non-conductive material on the pair of opposite side surfaces may be thicker than the coating of the non-conductive material on at least one of the inner or outer surfaces of the distal end portion.

In aspects, the blade and the main body may be coextruded.

In aspects, the main body may be flat and have a curved distal peripheral edge. The inner surface of the distal end portion may be concave and the outer surface of the distal end portion may be convex.

In aspects, the main body may include a long leg and a short leg extending perpendicularly from the long leg. The blade may extend inwardly from at least one of the long leg or the short leg.

In accordance with another aspect of the present disclosure, an electrosurgical electrode for coagulating and cutting tissue is provided and includes a main body fabricated from a conductive material and a conductive blade. The main body includes a linear segment and a arcuate segment extending from the linear segment, an inner surface, and an outer surface configured to coagulate tissue. The conductive blade extends from the inner surface of the main body. The conductive blade has a sharp edge configured to concentrate RF for cutting tissue.

In aspects, the conductive blade may project from the inner surface of the main body.

In aspects, the conductive blade may have a pair of opposite side surfaces converging toward the edge.

In aspects, the pair of opposite side surfaces may be coated with a non-conductive material.

In aspects, the edge may be devoid of the non-conductive material.

In aspects, the inner and outer surfaces of the main body may be coated with the non-conductive material.

In aspects, the coating of the non-conductive material on the pair of opposite side surfaces may be thicker than the coating of the non-conductive material on at least one of the inner or outer surfaces of the main body.

In aspects, the main body may be flat and have a curved distal peripheral edge. The inner surface of the main body may be concave and the outer surface of the main body may be convex.

In aspects, the main body may include a short leg extending perpendicularly from the linear segment. The arcuate segment may interconnect the linear segment and the short leg.

In aspects, the conductive blade may extend inwardly from at least one of the linear segment, the arcuate segment, or the short leg.

BRIEF DESCRIPTION OF THE DRAWINGS

Various aspects and features of the present disclosure are described hereinbelow with reference to the drawings wherein like numerals designate identical or corresponding elements in each of the several views:

FIG. 1 is a partial perspective view illustrating an electrosurgical electrode in accordance with an embodiment of the present disclosure;

FIG. 2 is an enlarged view of a distal end portion of the electrosurgical electrode of FIG. 1;

DETAILED DESCRIPTION

Figure 3:
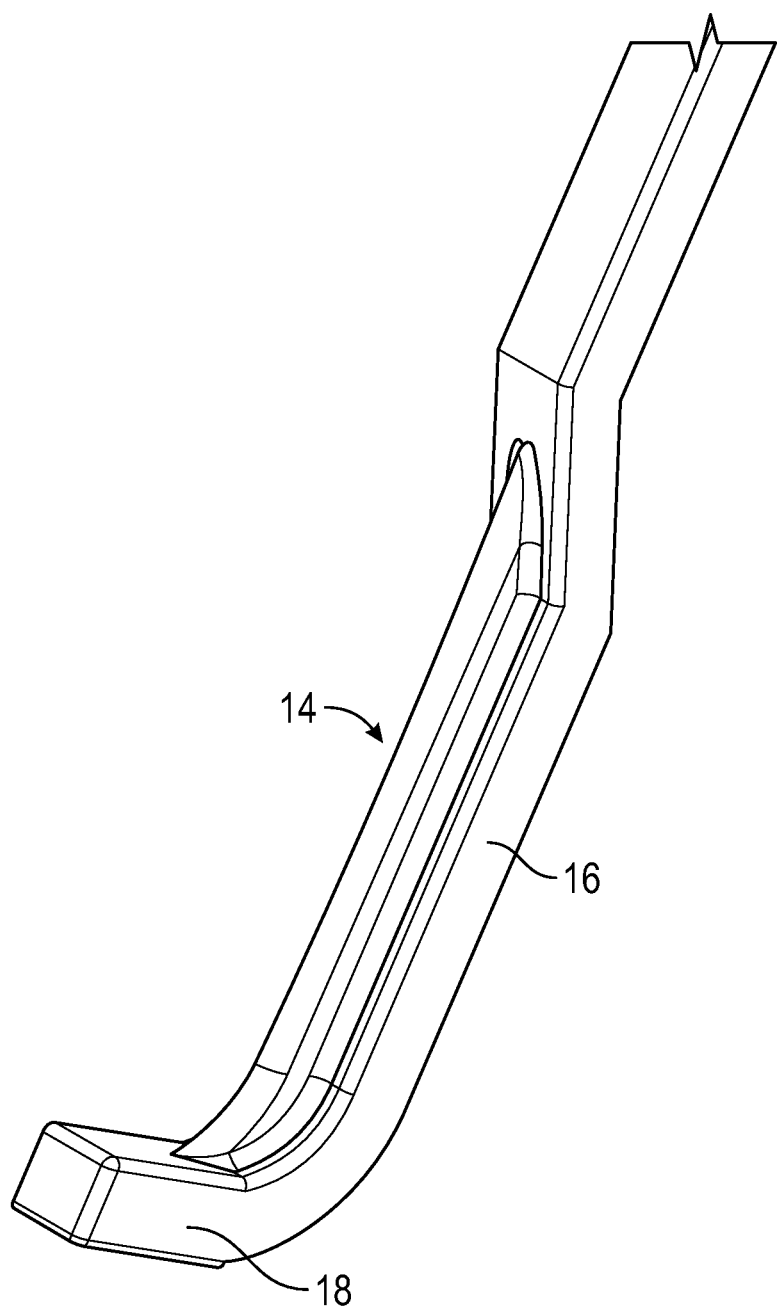
FIG. 3 is a partial perspective view illustrating an electrosurgical electrode in accordance with another embodiment of the present disclosure.

In an embodiment of the present disclosure, an RF concentration feature is electrically connected to the electrode but located on a surface not used for coagulation. The RF concentration feature may be metal and formed by a metal extrusion technique (e.g., co-extruded with the electrode) or any other suitable metal forming techniques such as, but not limited to, metal injection forming or metal 3D printing. The entire electrode may be coated with a non-stick coating to a particular thickness to maintain RF performance. However, along the sides of the RF concentration feature, the non-stick coating and/or a more isolative coating may be applied to provide a non-conductive surface. Features to this surface may also enable increased adherence or cohesion of the non-conductive coating such as surface treatment, convex features, or other designs to increase surface tension for the coating. A very small radius will be left exposed. This will end up concentrating RF energy on a thin isolated edge (e.g., radius of about 0.40 mm or less).

RF concentration produces minimal thermal damage with superior cutting ability at very low power levels. The limit of concentrating the RF on a thin edge is that the electrode no longer provides adequate hemostasis/coagulation power. These edges are located on surfaces that are not useful for general purpose RF application where coagulation is needed. During dissection procedures, the surgeon can often be seen tugging the tissue to get it the tissue to separate. The present disclosure provides for adding an RF concentration feature where edges are placed for enhancing the cutting ability of the laparoscopic electrode while not inhibiting the coagulation abilities of the electrode.

For example, in an embodiment of the present disclosure, an RF concentration feature is included on the internal edge of the hook where most of the hooking action on the device occurs. This additional feature would allow the surgeon to hook the tissue but, instead of tugging to achieve tissue separation, a small low power pulse of RF "CUT" or modified "CUT" mode activation would easily cut the tissue at the exposed edge of the feature. By doing so, the electrode now stays within the limited site of view of the laparoscopic camera as tugging often displaces the hook from the field of view. This also reduces trying to use a coagulation waveform to transect tissue which may cause unnecessary charring to the tissue and does not provide for as clean of a tissue transection as "CUT" mode does. Additionally, the RF concentration feature allows for the power level used for "CUT" mode to be reduced since the exposed edge of the feature focuses the RF energy for transecting.

An RF concentration feature can be added in a variety of locations without impacting the typical coagulation surfaces of the electrodes. For example, with a laparoscopic wire L-shaped hook electrode 10 (FIGS. 1-4) or a laparoscopic spatula electrode 100 (FIG. 5), the feature could be added to any suitable location (e.g., lower edge, upper edge, back edge, front edge, interior curvature, exterior curvature, etc.) on the electrode, as will be described in further detail below.

The present disclosure provides for an electrosurgical electrode having improved tissue transection performance without altering other key surfaces used for blunt dissection and hemostasis. Typically, the user drags the surfaces at the tip of the L-hook, or the edge of the spatula for blunt dissection. When the user desires hemostasis, the broader flat surfaces of the electrode are RF activated and placed in contact with the bleeding surface.

One dissection method uses the RF energy while tugging the tissue in the hook or across the broad curve surface of the spatula to transect the tissue. When doing this, the tissue doesn't always cleanly divide and/or unpredictable divides in the tissue may cause the electrode to touch adjacent tissue resulting in unintentional burns to the tissue surface. The surgeon may be unaware of the above-noted incident since the electrode may be out of the line of site of the surgeon.

In addition to the small RF active edge internal to the L-hook electrode or along the passive surface of the spatula electrode, additional functionality may now be added to the specific surfaces used more commonly for either dissection or hemostasis. The broad flat surfaces used for hemostasis can now have a thicker non-stick coating that enables them to have less eschar buildup and to be electrically active only when using specific coagulation waveforms (surface etching patterns or perforations on the coating can further enable this). Currently these surfaces are always RF hot when any surface of the electrode is being used. These surfaces are often not in the direct line of site of the surgeon, so it can cause inadvertent burns to tissue if accidentally resting up against tissue. The embodiments of the present disclosure would make the activation of the broader surface an intentional action. This can also be applied to monopolar scissors where all surfaces of the both blades are RF hot during activation. If the coatings were specifically designed so that the convex surface and bottom edges of the scissors were RF inert or RF active only on special coagulation modes, then inadvertent application of energy to tissue adjacent to the scissors could be mitigated without cumbersome solutions (like a silicon boot).

The present disclosure also provides for surfaces used only for blunt dissection to be designed to either allow greater RF current concentration for faster blunt dissection, or coated in such a manner as to not allow any RF to pass through the coated portion of the electrode. To further enhance the performance of those surfaces used only for blunt dissection, coatings and shapes may be added to enable dissection or hemostasis to be enhanced. Also, RF activation can then be controlled by specific surface design of the electrode.

With reference to FIGS. 1 and 2, an exemplary embodiment of an electrosurgical electrode 10 for coagulating and cutting tissue is illustrated. The electrode 10 includes a main body 12 and a conductive blade 14 attached to the main body 12. The main body 12 has a proximal end portion 12a configured to be coupled at its proximal end to a handle assembly (not explicitly shown) of a hand-held electrosurgical instrument, such as, for example, the handle assembly shown an described in U.S. Patent Application Publication No. 2011/0219887, filed on Jun. 23, 2010, the entire contents of which being incorporated by reference herein. The main body 12 is fabricated from a conductive material (e.g., steel, aluminum, copper, etc.) and includes a distal end portion 12b for coagulating and cutting tissue. The main body 12 is in electrical communication with an energy source, such as, for example, an RF energy source (not shown) for delivering a selected amount of RF energy to the main body 12.

The distal end portion 12b of the main body 12 has a long leg, such as, for example, a linear segment 16, a short leg 18, and a curved segment 20 interconnecting the long and short legs 16, 18. It is contemplated that the distal end portion 12b assumes an L-shaped configuration. However, other shapes and configurations for the distal end portion 12b are contemplated. The distal end portion 12b of the main body 12 has an inner surface 22, and an outer surface 24 disposed on an opposite side of the main body 12. The outer surface 24 is configured to coagulate tissue upon contact.

The conductive blade 14 extends or projects inwardly (e.g., in a direction away from the outer surface 24) from the inner surface 22 of the distal end portion 12b. The conductive blade 14 extends longitudinally along a longitudinal axis defined by the long leg 16. As shown in FIGS. 1 and 2, the conductive blade 14 extends along a distal section of the long leg 16, over the curved segment 20, and terminates before the short leg 18. In aspects, the conductive blade 14 may extend along any portion of the inner surface 22 of the main body 12. For example, with brief reference to FIG. 3, the conductive blade 14 may extend along an entire length of the long segment 16. As another example, with brief reference to FIG. 4, the conductive blade 14 may only extend along the length of the short leg 18.

With continued reference to FIGS. 1 and 2, the blade 14 has a pair of opposite side surfaces 14a, 14b converging in an edge 14c configured to concentrate RF for cutting tissue. In aspects, blade 14 may assume a triangular transverse cross-sectional configuration. The side surfaces 14a, 14b are coated with a non-stick and non-conductive material 28, such as, for example, polytetrafluoroethene. The edge 14c may be sharpened to facilitate cutting of tissue. In aspects, the edge 14c may be rounded or otherwise blunt. In aspects, the edge 14c may be devoid of the coating, such that the edge 14c functions as an exposed conductive and sharpened surface for concentrating RF energy. In aspects, the side surfaces 14a, 14b may have a thicker coating of the non-stick and non-conductive material than the outer surface 24 of the main body 12 or have a more insulative coating than the outer surface 24.

Figure 5:
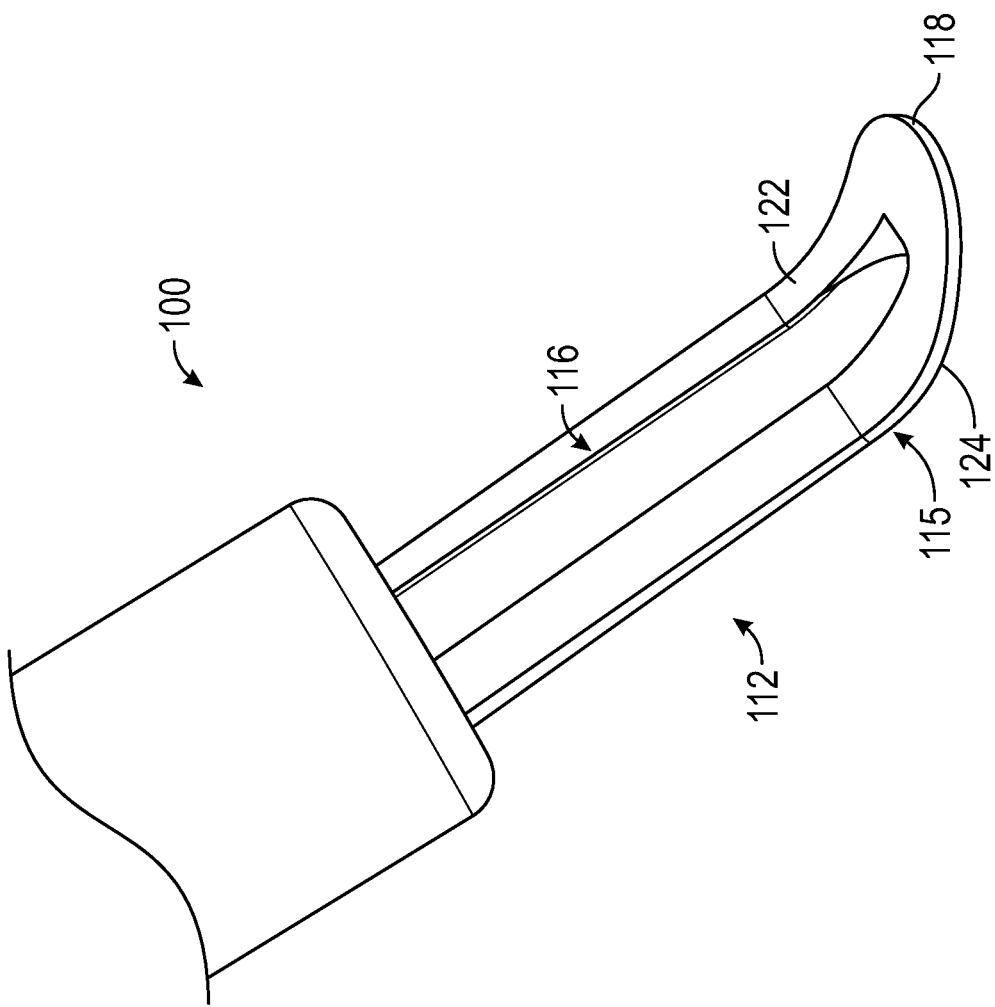
FIG. 5 is a partial perspective view illustrating an electrosurgical electrode in accordance with another embodiment of the present disclosure.
Figure 4:
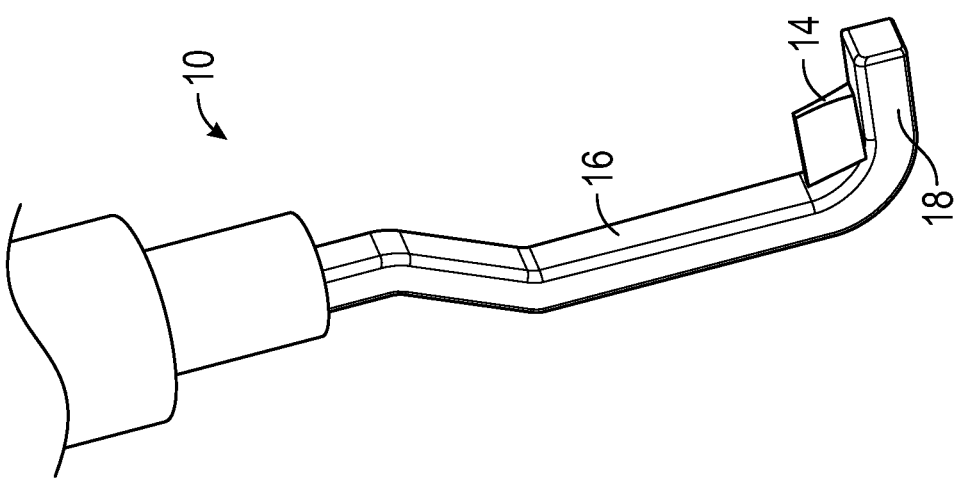
FIG. 4 is a partial perspective view illustrating an electrosurgical electrode in accordance with another embodiment of the present disclosure.

With reference to FIG. 5, another embodiment of an electrosurgical electrode 100 is illustrated, similar to the electrosurgical electrode 10. The electrosurgical electrode 100 includes a main body 112 and a blade 116 attached to the main body 112. The main body 112 is flat with an elongated oval configuration. The main body 112 has a curved distal end portion 115 defining a curved distal peripheral edge 118. The curved distal end portion 115 of the main body 112 has a concave inner surface 122 and a convex outer surface 124. The blade 116 projects inwardly from the concave inner surface 122.

The various embodiments disclosed herein may also be configured to work with robotic surgical systems and what is commonly referred to as "Telesurgery." Specifically, these features could be included on the 'end effectors' designed to interact laparoscopically with the tissue at the surgical site. Such robotic systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely controls the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions. As noted above, the RF concentration feature allows for the power level used for "CUT" mode to be reduced. By reducing the power level, the RF concentration feature may be beneficial to the added precision provided by a robotic system.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical electrode, comprising:
    an electrically conductive main body including:
        a curved segment;
        a first planar outer surface configured for tugging tissue; and
        a second planar outer surface, opposite the first planar outer surface, configured to coagulate the tissue; and
    an electrically conductive blade fixed to the first planar outer surface along at least the curved segment of the electrically conductive main body, the electrically conductive blade having a distal-most end extending from the first planar outer surface proximal to a distal-most end of the electrically conductive main body in a direction away from the second planar outer surface, the electrically conductive blade configured to cut the tissue being tugged by the first planar outer surface.

2. The electrosurgical electrode according to claim 1, wherein the electrically conductive main body includes a linear segment extending proximally from a proximal end of the curved segment, and the electrically conductive blade is fixed to the first planar outer surface along the linear segment and the curved segment.

3. The electrosurgical electrode according to claim 1, wherein the electrically conductive main body includes a distal linear segment extending distally from a distal end of the curved segment.

4. The electrosurgical electrode according to claim 3, wherein the electrically conductive blade is fixed to the first planar outer surface along the distal linear segment and the curved segment.

5. The electrosurgical electrode according to claim 1, wherein the second planar outer surface is configured to receive a first electrosurgical waveform for coagulating the tissue.

6. The electrosurgical electrode according to claim 5, wherein the electrically conductive blade is configured to receive a second electrosurgical waveform different than the first electrosurgical waveform for cutting the tissue.

7. The electrosurgical electrode according to claim 6, wherein the electrically conductive blade has a pair of opposite side surfaces converging toward an edge in a direction away from the second planar outer surface, the edge configured to concentrate electrosurgical energy from the second electrosurgical waveform for cutting the tissue.

8. The electrosurgical electrode according to claim 7, wherein the pair of opposite side surfaces are coated with a non-conductive material.

9. The electrosurgical electrode according to claim 1, wherein the electrically conductive blade and the electrically conductive main body are coextruded.

10. The electrosurgical electrode according to claim 1, wherein the curved segment has a curved peripheral edge defining a distal-most end of the electrosurgical electrode.

11. The electrosurgical electrode according to claim 1, wherein the first planar outer surface along the curved segment is concave and the second planar outer surface along the curved segment is convex.

12. An electrosurgical electrode, comprising:
a curved segment;
a first outer surface extending along the curved segment, the first outer surface configured for tugging tissue;
a second outer surface, opposite the first outer surface, configured for coagulating the tissue; and
a blade fixed to the first outer surface along at least the curved segment, the blade having an edge configured to concentrate RF energy for cutting the tissue, wherein the blade has a distal-most end extending from the first outer surface proximal to a distal-most end of the first outer surface in a direction away from the second outer surface.

13. The electrosurgical electrode according to claim 12, further comprising a linear segment extending proximally from a proximal end of the curved segment, wherein the blade is fixed to the first outer surface along the linear segment and the curved segment.

14. The electrosurgical electrode according to claim 12, further comprising a distal linear segment extending distally from a distal end of the curved segment.

15. The electrosurgical electrode according to claim 14, wherein the blade is fixed to the first outer surface along the distal linear segment and the curved segment.

16. The electrosurgical electrode according to claim 12, wherein the curved segment has a curved peripheral edge defining a distal-most end of the electrosurgical electrode.

17. The electrosurgical electrode according to claim 12, wherein the first outer surface along the curved segment is concave and the second outer surface along the curved segment is convex.

18. An electrosurgical electrode, comprising:
an electrically conductive main body including:
a curved segment;
a first planar outer surface configured for tugging tissue; and
a second planar outer surface, opposite the first planar outer surface, configured to receive a first electrosurgical waveform for coagulating tissue; and
a blade fixed to the first planar outer surface along at least the curved segment and configured to receive a second electrosurgical waveform different than the first electrosurgical waveform, wherein the blade has a distal-most end that projects from the first planar outer surface proximal to a distal-most end of the electrically conductive main body in a direction away from the second planar outer surface to form an edge configured to concentrate electrosurgical energy from the second electrosurgical waveform for cutting the tissue.

19. The electrosurgical electrode according to claim 18, further comprising a linear segment extending proximally from a proximal end of the curved segment, wherein the blade is fixed to the first planar outer surface along the linear segment and the curved segment.

20. The electrosurgical electrode according to claim 18, further comprising a distal linear segment extending distally from a distal end of the curved segment, wherein the blade is fixed to the first planar outer surface along the distal linear segment and the curved segment.

* * * * *